United States Patent
Renlund

(10) Patent No.: US 9,949,679 B2
(45) Date of Patent: Apr. 24, 2018

(54) MICROFABRICATED SENSOR AND A METHOD OF SENSING THE LEVEL OF A COMPONENT IN BODILY FLUID

(71) Applicant: Ascilion AB, Kista (SE)

(72) Inventor: Markus Renlund, Åkersberga (SE)

(73) Assignee: Ascilion AB, Kista (SE)

(*) Notice: Subject to any disclaimer, the term of this patent is extended or adjusted under 35 U.S.C. 154(b) by 385 days.

(21) Appl. No.: 14/649,422

(22) PCT Filed: Nov. 29, 2013

(86) PCT No.: PCT/SE2013/051416
§ 371 (c)(1),
(2) Date: Jun. 3, 2015

(87) PCT Pub. No.: WO2014/088493
PCT Pub. Date: Jun. 12, 2014

(65) Prior Publication Data
US 2015/0313527 A1 Nov. 5, 2015

(30) Foreign Application Priority Data
Dec. 7, 2012 (SE) .................................... 1200754

(51) Int. Cl.
*A61B 5/00* (2006.01)
*A61B 5/15* (2006.01)
(Continued)

(52) U.S. Cl.
CPC ...... *A61B 5/150282* (2013.01); *A61B 5/0507* (2013.01); *A61B 5/14514* (2013.01);
(Continued)

(58) Field of Classification Search
USPC ......................................................... 600/365
See application file for complete search history.

(56) References Cited

U.S. PATENT DOCUMENTS

2002/0169411 A1* 11/2002 Sherman ........... A61M 37/0069
604/24
2003/0153900 A1 8/2003 Aceti et al.
(Continued)

FOREIGN PATENT DOCUMENTS

| EP | 1 820 441 A1 | 8/2007 |
| EP | 2 458 368 A1 | 5/2012 |
| WO | WO 03/030731 A1 | 4/2003 |

OTHER PUBLICATIONS

Pavuluri, S. K., et al. "Integrated microfluidic capillary in a waveguide resonator for chemical and biomedical sensing." Journal of Physics: Conference Series. vol. 178. No. IOP Publishing, 2009.*

*Primary Examiner* — Christian Jang
*Assistant Examiner* — Mitchell E Alter
(74) *Attorney, Agent, or Firm* — Blank Rome LLP

(57) ABSTRACT

The disclosure relates to a microfabricated sensor (1) comprising at least one hollow microneedle (2) for minimal invasive extraction of a sample of bodily fluid, a fluid channel (3) connected to the at least one microneedle for receiving a sample of bodily fluid extracted by the at least one microneedle, a microwave transmission line (4) coupled to and extending along at least a portion of the fluid channel, such that the dielectric properties of the fluid in the fluid channel provide an influence on the electrical properties of the transmission line. The disclosure further relates to a method of microfabricating such a sensor and a method of sensing the level of a component in bodily fluid of a patient by providing such a sensor.

34 Claims, 4 Drawing Sheets

(51) Int. Cl.
*A61B 5/145* (2006.01)
*A61B 5/05* (2006.01)
*A61B 10/00* (2006.01)
*A61B 5/151* (2006.01)

(52) U.S. Cl.
CPC ...... *A61B 5/14525* (2013.01); *A61B 5/14532* (2013.01); *A61B 5/150351* (2013.01); *A61B 5/150984* (2013.01); *A61B 5/6826* (2013.01); *A61B 10/0045* (2013.01); A61B 5/150022 (2013.01); A61B 5/150068 (2013.01); A61B 5/15105 (2013.01); A61B 5/15186 (2013.01); A61B 5/150389 (2013.01); A61B 5/150503 (2013.01); A61B 2010/008 (2013.01); A61B 2562/125 (2013.01)

(56) References Cited

U.S. PATENT DOCUMENTS

| | | | |
|---|---|---|---|
| 2005/0171480 A1* | 8/2005 | Mukerjee | A61M 37/0015 604/173 |
| 2005/0209565 A1* | 9/2005 | Yuzhakov | A61M 37/0015 604/173 |
| 2007/0161964 A1* | 7/2007 | Yuzhakov | A61M 37/0015 604/272 |
| 2008/0221408 A1 | 9/2008 | Hoarau et al. | |
| 2011/0096327 A1* | 4/2011 | Papautsky | B01D 21/0087 356/335 |
| 2012/0041337 A1* | 2/2012 | Ferguson | A61M 37/0015 600/573 |

* cited by examiner

MICROFABRICATED SENSOR AND A METHOD OF SENSING THE LEVEL OF A COMPONENT IN BODILY FLUID

TECHNICAL FIELD

The present invention relates generally to a microfabricated sensor and a method of sensing the level of a component in bodily fluid.

BACKGROUND ART

Glucose monitoring is part of an everyday life, especially for diabetic individuals. To accommodate normal life, diabetic individuals need to accurately and frequently measure the glucose level in the body, preferably in a small amount of body fluid. The most common method to determine the blood glucose level is to use disposable glucose test strips and a glucose meter, see U.S. Pat. No. 5,951,836. To extract blood, a lancet pricks the finger and a drop of blood is placed on the strip. The main drawback with the glucose test strips is the pain from the extraction of blood using the lancet as well as the skin damage.

Other methods to measure the glucose level have been suggested in the prior art. The main goal is to develop a non-invasive method ("see The Pursuit of Noninvasive Glucose: Hunting the Deceitful Turkey", John L. Smith, Second edition 2011). Measurement techniques range from spectroscopic, optical, light scattering, breath and transdermal techniques. Techniques fail primarily due to difficulties to obtain an accurate glucose measurement. It has been shown that the glucose level in interstitial fluid (ISF) correlates well to the blood glucose level (Suresh et al. "Comparison of glucose concentration in interstitial fluid, and capillary and venous blood during rapid changes in blood glucose levels", Vol 3, No 3, 2001, Diabetes Technology and Therepeutics).

The use of microtechnology to reduce the size of needles to minimize discomfort is a rapidly developing arena of investigation for the transcutaneous delivery of drugs. Such microneedles have been developed for extracting ISF transdermal, see U.S. Pat. No. 7,753,888.

SUMMARY OF INVENTION

An objective of the present invention is to provide a sensor for detecting a component in bodily fluid, where the sensor provides for a rapid and accurate detection of a component in bodily fluid.

Thus the invention relates to a microfabricated sensor comprising at least one hollow microneedle for extraction of a sample of bodily fluid, a fluid channel connected to the at least one microneedle for receiving a sample of bodily fluid extracted by the at least one microneedle, a microwave transmission line coupled to and extending along at least a portion of the fluid channel, such that the dielectric properties of the fluid in the fluid channel provide an influence on the electrical properties of the transmission line.

Thereby a sensor for detecting a component in bodily fluid is provided, which sensor provides for a rapid and accurate detection of a component in bodily fluid, such as ISF or blood. The microfabricated sensor may be integrated in hand held devices. There may also be minimal damage to biological tissues at the point of entrance of the microneedle, and the discomfort of the patient may be reduced.

The microwave transmission line may extend along the full length of the fluid channel, thus increasing the sensitivity of the device.

The at least one microneedle may comprise a capillary bore, e.g. a single capillary bore. Thereby bodily fluid may be extracted by means of capillary suction. Alternatively, or in addition, a suction force may be applied to the fluid channel and the at least one hollow microneedle to extract bodily fluid.

The at least one microneedle may be provided with a cap at a distal end for shielding the capillary bore from clogging, whereby at least one opening to the capillary bore is provided in a lateral direction of the microneedle, perpendicular to the axial or longitudinal extension of the microneedle.

A plurality of openings may be provided in a lateral direction, around a circumference of the microneedle. The at least one opening may be provided about midways along a longitudinal extension of the microneedle. Thereby the extraction of bodily fluid is facilitated and the risk for clogging is further reduced.

The capillary bore of the at least one microneedle may be provided with a hydrophilic surface. Thereby capillary suction of bodily fluid may be assisted.

The microneedle may comprise a plurality of cutting elements extending along a longitudinal direction of the microneedle. Thereby the skin may be cut and opened to facilitate extraction of bodily fluid.

The at least one microneedle may have a length of 200-1000 µm, preferably 400-900 µm, more preferably 500-600 µm, and an outer diameter of 50-200 µm, preferably 80-150 µm. Thereby the microneedle has dimensions suitable for penetration of the skin and extraction of bodily fluid.

The fluid channel may have an extension in a channel plane, and wherein the microneedles protrude in a direction perpendicular to the channel plane.

The fluid channel may comprise a spiral channel portion. Alternatively or additionally the fluid channel may comprise a meander portion. Thereby the fluid channel may be provided with a certain length to achieve high measurement accuracy, but with a limited footprint to decrease cost of manufacture.

The spiral portion may be a continuous interlaced double spiral. Thereby a first and second end portion may be accessed at a radially outer portion of the spiral.

The central portion may be S-shaped.

The at least one microneedle may be arranged at and connected to a central portion of the spiral channel portion. Thereby the fluid channel may be filled with bodily fluid from the central portion and outward, preferably in two directions of the channel simultaneously.

The fluid channel may be provided with a hydrophilic surface. Thereby capillary suction of bodily fluid may be assisted.

The sensor may comprise a plurality of hollow microneedles. Thereby the filling of the fluid channel with bodily fluid may be optimized.

The microneedles may be distributed along a portion of the channel, preferably a central portion of the channel.

The microwave transmission line may be a coplanar waveguide, a stripline, microstrip or a partially or fully enclosed cavity where the enclosure comprises an electrical conductive material and the cavity is formed such that it has an electrical conductor placed inside in a way that there is no direct contact between the enclosure and the conductor.

The fluid channel may form a RF (i.e. radiofrequency, microwave) cavity of the microwave transmission line.

The microwave transmission line may comprise a spiral transmission line portion. Thereby the footprint of the sensor may be limited.

The microwave transmission line may be configured for transmission mode RF spectroscopy. Thereby measurements of the dielectric properties of bodily fluid in the fluid channel may be performed in a simple manner.

The fluid channel may have a width and/or height in the range of 10-100 µm, preferably in the range of 25-75 µm. Thereby the capillary and fluidic properties of the channel may be optimal.

The fluid channel may have a length in the range of 1-50 mm, preferably in the range of 20-40 mm. Thereby the measurement accuracy of the sensor may be high enough.

The fluid channel may be microfabricated in a channel plate, preferably a silicon wafer. The at least one microneedle may be fabricated in the channel plate, preferably in silicon.

Thereby the sensor may be formed by silicon micromachining, resulting in a high dimensional accuracy of the structures of the sensor, formed in a material suitable for biomedical devices having very good mechanical properties, and suitable for batch fabrication.

The at least one microneedle may be at least partly surrounded by a frame structure dimensioned to support the tip of a finger. The frame structure dimensioned to support the tip of a finger may be a ring shaped structure protruding along the longitudinal direction of the at least one microneedle. Thereby the skin may be stretched by the supporting structure, such that penetration of the microneedles through the skin is facilitated.

The microwave transmission line may be fabricated in a transmission line substrate plate, preferably a glass wafer or a silicon wafer.

The microfabricated sensor may be a glucose sensor.

The invention further relates to a method of microfabricating a sensor as disclosed herein, comprising
providing a channel wafer, having a first and a second face,
etching the at least one microneedle on the channel wafer, protruding from the first face of the silicon wafer,
etching the fluid channel in the second face of the channel wafer,
providing a transmission line substrate wafer,
forming the microwave transmission line on the transmission line substrate wafer,
assembling the channel wafer and the transmission line substrate wafer such that the microwave transmission line is coupled to and extending along at least a portion of the fluid channel.

Thereby a sensor for detecting a component in bodily fluid is provided, which sensor is minimally invasive and provides for a rapid and accurate detection of a component in blood. The method allows for a microfabricated sensor which may be manufactured at reduced cost.

The transmission line may be formed to provide two electrical ports, one input port and one output port, with electrical contacts, that may contain any combination of ground and two signals, most preferably a geometrical structure of ground-signal-ground-signal-ground or ground-signal-signal-ground. Ground and signal contacts may be made by means of wire bonding, ribbon bonding, probing, connectors and/or conductive epoxy to read out electronics.

The channel wafer may be a silicon wafer and the transmission line substrate wafer may be a glass wafer, which wafers are assembled by bonding.

The microneedles may be formed in the channel wafer by a deep reactive ion etching, possibly combined with wet etching. Thereby fine structures, such as the microneedle may be microfabricated in the silicon material.

The invention further relates to a method of detecting and/or measuring a component in bodily fluid of a patient comprising
providing a microfabricated sensor as disclosed herein,
extracting a sample of bodily fluid by means of the at least one hollow microneedle,
receiving the fluid sample in the fluid channel,
performing an swept frequency or pulsed measurement on the fluid sample by means of the microwave transmission line, and
detecting and/or measuring the component based on the performed swept frequency or pulsed measurement.

Thereby a component in bodily fluid may be rapidly and accurately detected and/or measured by a minimally invasive method using the sensor as disclosed herein.

The method may comprise determining the level of the component based on the performed swept frequency or pulsed measurement.

The measurement may comprise injecting an input electrical signal at a first end of the transmission line and detecting an output signal at a second end of the transmission line.

The swept frequency or pulsed measurement may comprise detecting and/or measuring a phase change in an electrical signal.

The fluid channel may be configured such that the electrical phase as a function of the frequency of the electrical signal changes proportionally in respect to certain components within the bodily fluid The swept frequency measurement may comprise detecting and/or measuring a phase change in the electrical signal as being dependent on the concentration of a component in the bodily fluid. The electrical signal may be inserted at a first end of the transmission line and the phase change may be detected at a second end of the transmission line.

The swept frequency measurement may be performed with a center frequency above 1 GHz, preferably above 4 GHz, more preferably above 8 GHz.

The pulsed measurement may be performed by injecting a pulse, which may have a pulse width of less than 1 ns, preferably less than 100 ps, in a first end of the transmission line and conducting a Fourier transform or fast Fourier transform (FFT) of the output signal on a second end of the transmission line. The measurement may comprise a comparison of the input and output signal thus detecting the complex portions of the signal in order to detect and/or measure the concentration of components in bodily fluid The pulse may be a square pulse with a known or unknown amplitude.

The bodily fluid may be blood and/or interstitial fluid.
The component may be glucose.

BRIEF DESCRIPTION OF DRAWINGS

The invention is now described, by way of example, with reference to the accompanying drawings, in which.

DESCRIPTION OF EMBODIMENTS

Figure 1:
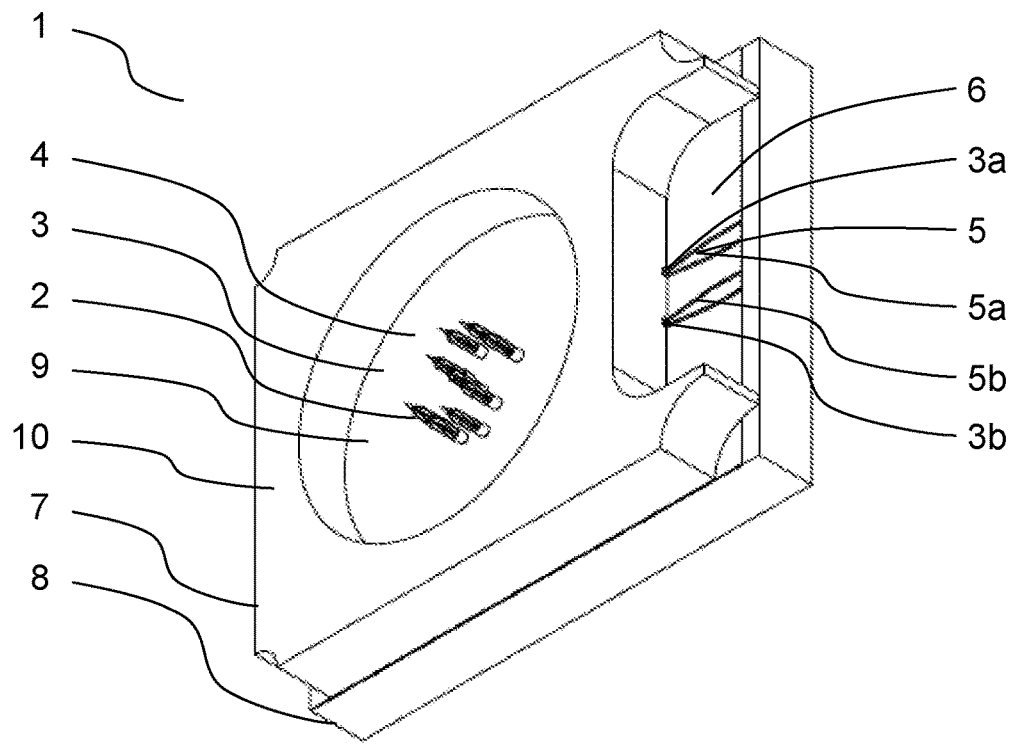
FIG. 1 shows a microfabricated sensor in perspective view.
Figure 2:
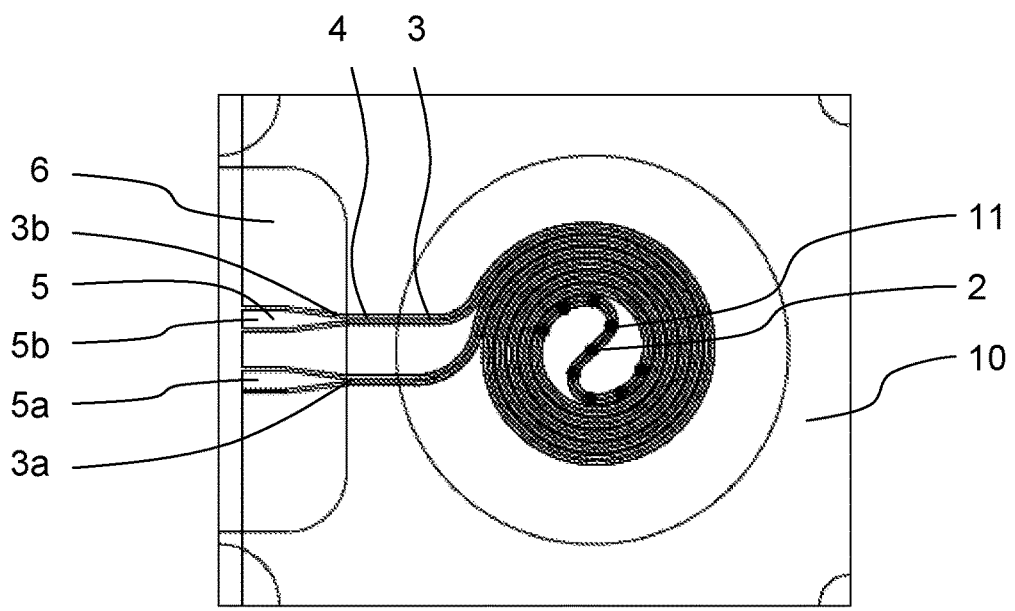
FIG. 2 shows a microfabricated sensor in a cross-sectional view showing fluid channel and transmission line.

In FIGS. 1 and 2, a microfabricated sensor 1 is shown comprising a plurality of hollow microneedles 2 for minimal invasive extraction of a sample of bodily fluid. The microneedles each comprises a single capillary bore, and the sensor further comprises a fluid channel 3 (not visible in FIG. 1, see e.g. FIG. 2) connected to the microneedles for receiving a sample of bodily fluid extracted by the microneedles. The fluid channel is open to the ambient through a first 3a and a second 3b fluid channel opening to enable capillary suction of the bodily fluid. The term minimally invasive implies that there is minimal damage to biological tissues at the point of entrance of the microneedles, thus reducing the discomfort of the patient.

The sensor further comprises a microwave transmission line 4 (not visible in FIG. 1, see e.g. FIG. 2) coupled to and extending along at least a portion of the fluid channel, such that the dielectric properties of the fluid in the channel provide an influence on the electrical properties of the transmission line. The microwave transmission line 4 comprises a center conductor 5, electrically connected by a first 5a and a second 5b electrical contact pad, forming a first and a second electrical port of the transmission line, and a ground plane 6. The contact pads 5a, 5b and a contact pad of the ground plane 6 are positioned on an edge portion of the sensor to facilitate electrical connection of the sensor.

The sensor is formed by a channel plate 7 and a substrate plate 8, bonded together. The channel plate supports the plurality of microneedles 2 protruding from a microneedle support surface 9 of the channel plate. The fluid channel 3 is formed in the opposite surface of the channel plate as compared to the microneedle support surface. The microneedles protrude in a direction perpendicular to the microneedle support surface and a channel plane, in which the fluid channel extends.

A ring shaped frame structure 10 surrounds the microneedles. The inner diameter of the ring shaped structure is in the range of 1-10 mm and is thus dimensioned to support the tip of a finger. The tips of the microneedles are protected by the upper surface of the ring shaped frame structure, such that they do not protrude beyond this upper surface. Thus the needles are protected from breakage during fabrication and handling of the sensor, and the sensor may be sealed by a protective film during fabrication and handling. The ring shaped structure has the effect that the skin of the tip of a finger pressed towards the microneedles may be brought into tension, thereby facilitating the penetration of the microneedles through the skin.

Turning to FIG. 2, the fluid channel 3 and transmission line 4 is shown in a cross-section between the channel plate and the substrate plate. As shown in the figure, the fluid channel and transmission line co-extend and comprises the form of a double spiral shape having an S-shaped center portion 11 where the shape turn from a first spiral portion of the double spiral, to a second spiral portion of the double spiral. The spiral portion of the fluid channel defines a channel plane.

Figure 3A:
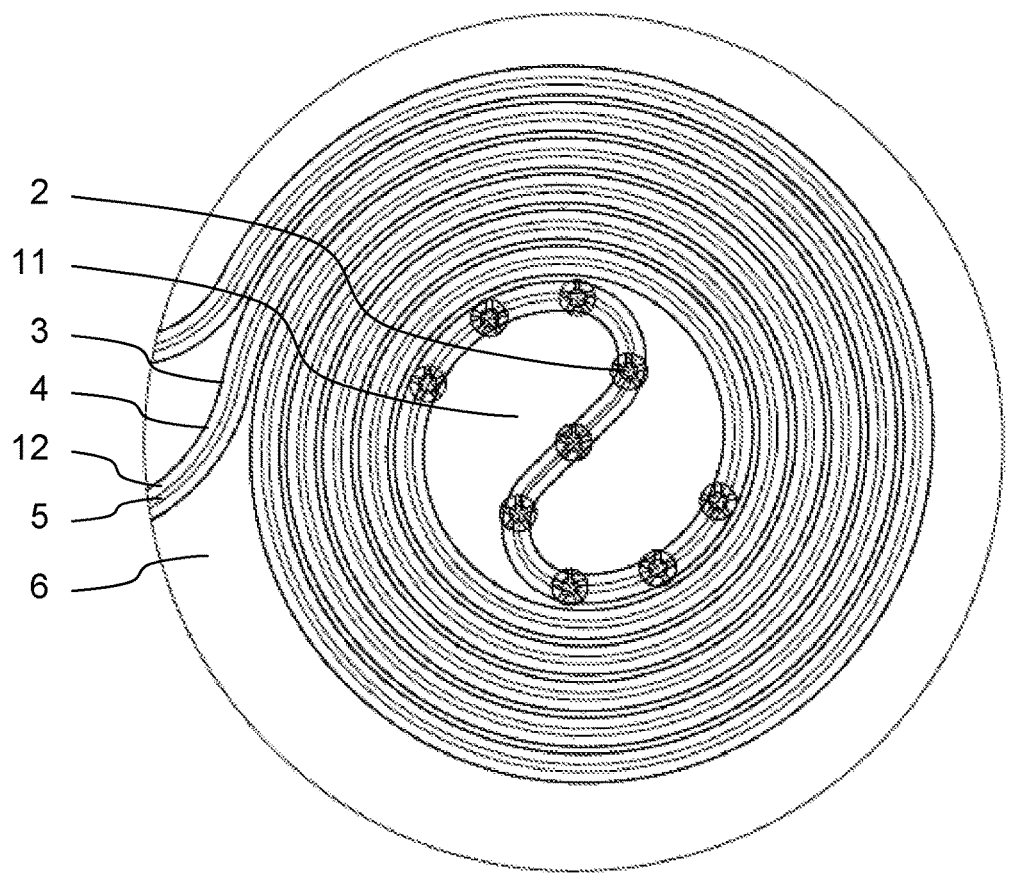
FIG. 3a shows a central portion of the fluid channel and transmission line.

The spiral portion of the fluid channel 3 and the transmission line 4 is further disclosed in FIG. 3a. The transmission line comprises a center connector 5 electrically separated from the ground plane 6 by means of isolating tracks 12 on each side of the center connector. The fluid channel 3 typically has a rectangular cross-section, but the cross-section may alternatively be e.g. triangular or semi-circular.

A plurality of microneedles, in this case nine microneedles, are connected to the S-shaped center portion of the fluid channel, distributed over this center portion at a distance from each other, to facilitate penetration of the skin.

The fluid channel length is typically about 30 mm, e.g. 10-50 mm, preferably 20-40 mm. This is a trade-off between a longer channel provides for an increasing measuring accuracy, and a shorter channel provides for a smaller footprint and thus a reduced cost of manufacture.

Figure 3B:
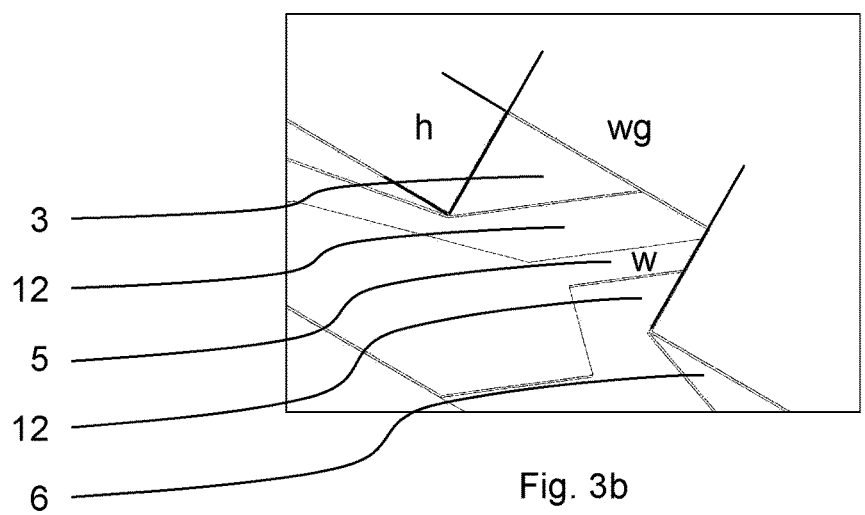
FIG. 3b shows a perspective view of the fluid channel and transmission line.

In FIG. 3b a perspective view of a fluid channel entry 3a/3b and the connectors forming the transmission line are shown. The width wg of the fluid channel, in the channel plane, is typically about 50 µm, and the height h of the fluid channel, out of the channel plane, is typically 50 µm. These cross-sectional dimensions provide for suitable fluidic and capillary properties as well as suitable electrical properties of the transmission line in the frequency region described herein of the fluid channel/RF cavity.

The channel walls are coated with an electrical conductor, e.g. gold, connected to the ground plane 6 and forming part of the ground conductor in the transmission line formed along the channel. The width w of the center conductor 5 is about 20 µm, and the width of each insulting track 12 is thus about 15 µm. The fluid channel thus forms a RF cavity of the transmission line.

Figure 4:
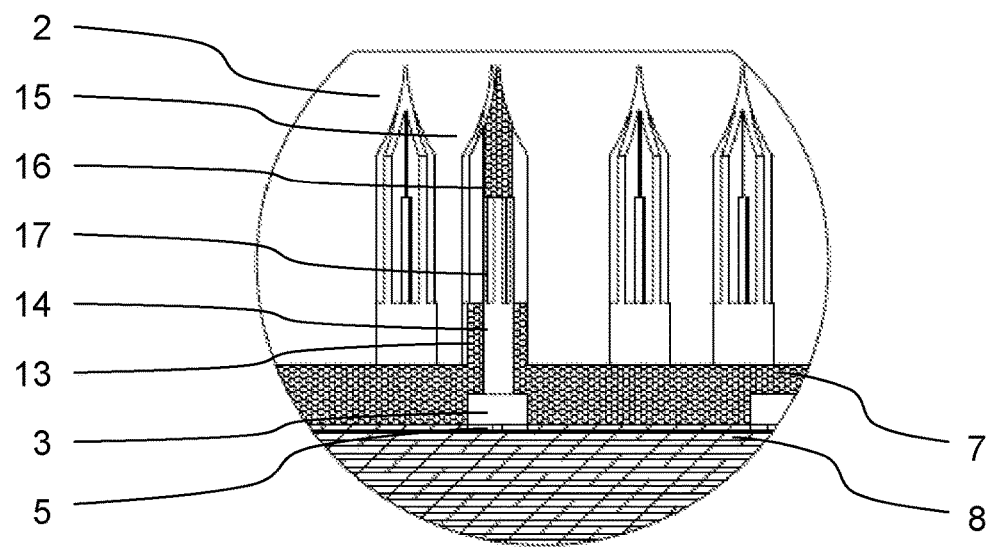
FIG. 4 shows a cross-sectional view of a microneedle of the sensor.

In FIG. 4 a cross-section of one of the microneedles 2 is shown supported by the channel plate 7 forming the fluid channel 3. The substrate plate 8 connected to the channel plate is further shown, supporting the center connector 5 of the transmission line. The microneedle comprises a base portion 13 forming the base of the needle connected to the channel plate. The base forms within itself a capillary bore 14 in fluid transferring contact with the fluid channel 3. The microneedle has a longitudinal extension in the protruding direction, and comprises a tip portion 15 at distal end of the needle. The tip portion comprises a cap 16 for shielding the capillary bore from clogging during penetration. A plurality of openings 17 are provided in several lateral directions around the circumference of the microneedle, about midways along the longitudinal direction of the microneedle.

Figure 5:
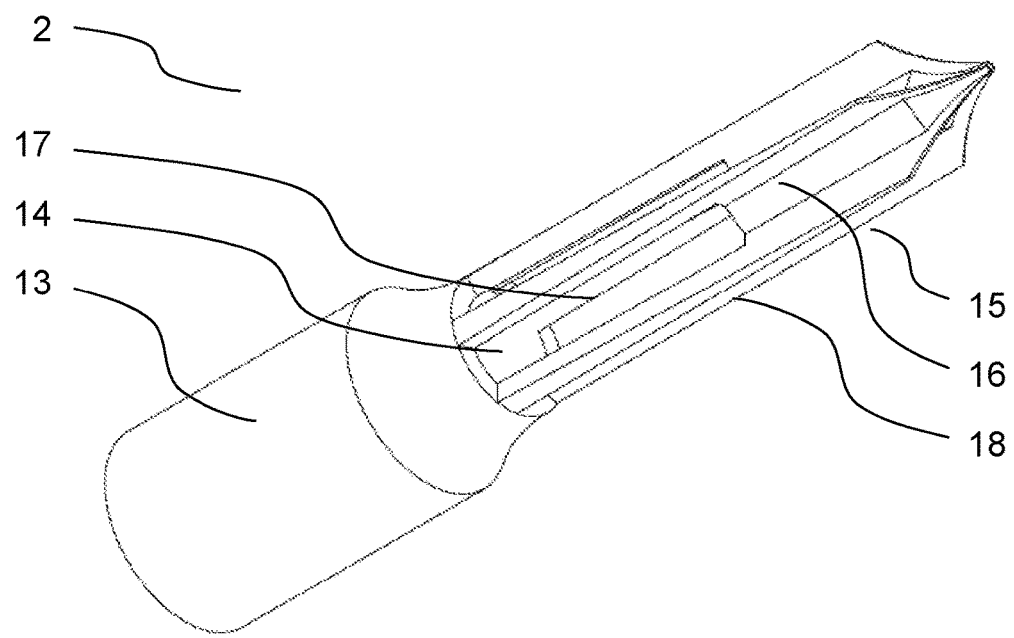
FIG. 5 shows a perspective view of a microneedle of the sensor.

An example of a microneedle 2 is further shown in FIG. 5. The microneedle has an elongated shape with a base portion 13 and a tip portion 15. The base portion is cylindrical and forms a capillary bore 14. The base portion has a diameter that may be narrowed down in a direction towards the tip. The tip portion comprises a cap 16 for shielding the capillary bore. The tip portion is supported in the base portion by a set of elongated elements 18 forming a plurality of openings 17 around the circumference of the microneedle. These elongated elements extend along the longitudinal direction of the microneedle and also functions as cutting elements for cutting the skin.

Figure 6:
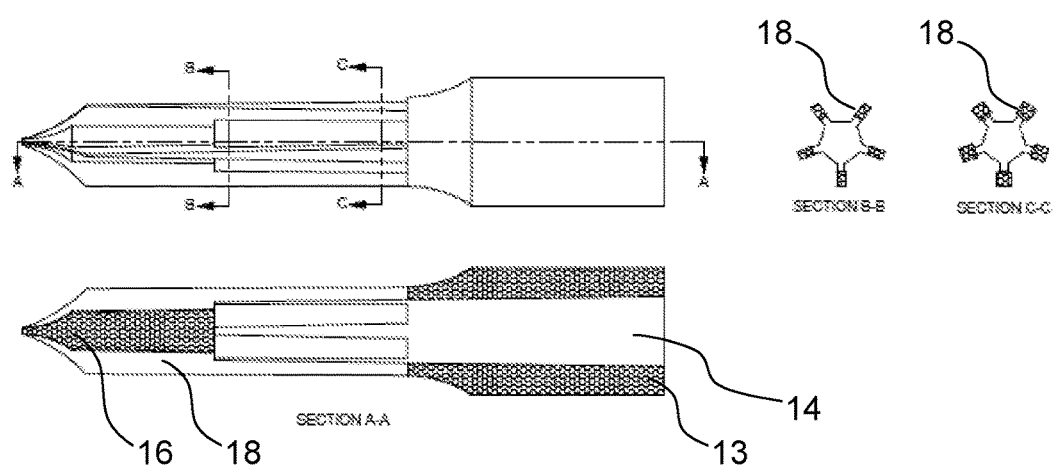
FIG. 6 shows various cross-sectional views of a microneedle of the sensor.

In FIG. 6 a microneedle is shown in three different cross-sections A-A, B-B and C-C. In cross-section A-A the base portion 13 is shown to form a capillary bore 14 for transporting fluid to the fluid channel. The cap 16 is supported by a plurality of elongated elements 18. In the example shown the number of elongated elements is 5, but the number of elongated elements may be in the range of 2-20. In sections B-B and C-C it is shown that the elongated elements are narrowed down towards the tip portion of the microneedle to form cutting elements for cutting the skin during penetration.

During operation, the tip of a finger is pressed towards the microneedles 2 and supported by the ring-shaped frame structure 10. The skin is then stretched by the supporting structure, such that penetration of the microneedles through the skin is facilitated. The microneedles are penetrated into the skin by cutting the skin by means of the sharp tip portion of the needle, and by means of the elongated cutting elements 18. Bodily fluid in or underneath the skin of the finger is extracted by means of the plurality of openings 17 of the microneedles. The bodily fluid may be e.g. blood or interstitial fluid. The bodily fluid is extracted by capillary suction forces into the capillary bore 14. The cap 16 reduces the risk of the capillary bore of the microneedles are clogged by tissue material from the finger.

The bodily fluid extracted by the microneedles is transported by capillary action into the spiral portion of the fluid channel 3 where it forms a dielectric medium in the RF transmission line, in contact with the central conductor 5 and the ground plane 6 in the fluid channel.

The RF transmission line is configured for transmission measurements. In an alternative configuration, the RF transmission line may be configured for reflection measurements of the properties of the transmission line. In this alternative configuration the transmission line is provided with a termination resistance at the reflection end of the transmission line (i.e. the central portion of the spiral). The dielectric properties of the bodily fluid received in the fluid channel may be analysed by means of analyzing the RF signal in the phase domain to identify changes in the phase.

The RF measurement may be performed at a center frequency above 1 GHz, preferably above 4 GHz, more preferably above 8 GHz. In one example the RF measurement is performed at a center frequency of 8 GHz. By performing the measurement at high frequency, the measurement accuracy may be high.

The RF measurement may be performed by injecting an electrical signal of constant amplitude into the input port, i.e. the first port 5a. The frequency is swept with a center frequency, e.g. above 1 GHz, preferably above 4 GHz, more preferably above 8 GHz, and with a sweep range preferably less than 10 GHz.

The phase of the output signal, i.e. on the second port 5b, may be correlated to and well determined in respect to an empty fluid channel and or a fluid channel filled with a fluid consisting of know concentrations of the component of interest. A phase change when using an unknown but similar substance will therefore be due to a different concentration of the component of interest in the substance and the concentration of the component of interest may be calculated as it is proportional to the phase of the output signal of an empty fluid channel with an offset as well as proportional to a previously calibrated fluid channel of the same geometry filled with an known substance of similar content.

The phase as a function of the frequency of the electrical signal injected in one end of the transmission line of an empty fluid channel or a fluid channel filled with a known substance may be determined by theoretical calculations, wafer test or unit test in such way that it may be used as means of calibration.

Thereby the presence or concentration of a component in the bodily fluid may be analysed by means of the disclosed sensor. According to one preferred alternative, the component is glucose, whereby the sensor may be used to determine the glucose level in an individual.

In the following, a method of microfabricating a sensor is described.

Microfabrication is defined to include fabrication techniques of structures in the micrometer range. The final components can be in the order of millimeter, and even centimeter, including feature sizes down to sub-micrometers. Micromachining may include one or more of lithography, wet etching, dry etching (such as deep reactive ion etching, DRIE) etc, but may further include one or more of electron or ion bean machining, plasma beam machining, laser machining, electro discharge machining, micromilling, micromolding, microreplication in a polymer, micro solid freeform fabrication, micro stereo lithography, electroplating and the like. Micromachining allows for a miniaturised device that may be batch fabricated and thus produced at a reduced cost.

The lithographic steps of the method of microfabricating the sensor are performed similarly, and therefore described firstly. The first step in the lithography is to prime the wafers in a HMDS oven. This gives a better adhesion for the resist, which is later coated on the wafer. As a side effect, the wafer will also be hydrophobic.

The next step in the lithography is the resist coating, such as with a positive resist.

The following step in the lithography is to create the pattern on the wafer, so the etching pattern may be created later. A mask for the different etching structures and the wafer is exposed with UV light creating a pattern in the resist. The resist (with the pattern) works as a mask during the etching, this allows the wafer to be etched and only the wanted pattern is created and the resist protect the rest of the surface.

The pattern of the resist is thereafter developed and hard baked. The purpose of hard baking is to remove residual solvent and to improve the adhesion of the resist so it will protect the wafer enough.

After silicon etching, a resist stripping step is carried out to remove the resist and to access the next mask. This is advantageous, since one mask may be removed and another silicon etching may be carried out with an oxide mask that is covered by the previous resist mask.

Oxide stripping is done by dipping the wafer in 50% HF and is done to remove the oxide layer. When forming the needles, oxidation and oxide stripping may be repeated until a sharp enough tip of the needle is created.

The oxide etchings are carried out to create an oxide mask, since a resist mask may not be done after a first silicon etching. Therefore, the second etch patterns is created by resist followed by oxide etch before the first etch pattern is created by resist. An oxide etch is also carried out to remove the oxide from the wafer, were the silicon etch needs to take place afterwards.

The silicon etch creates the actually needles, the fluid channel and the frame structure. The structures are etched in an Inductively Coupled Plasma (ICP) Deep Reactive Ion Etching (DRIE) apparatus.

To produce the needles and fluid channel, wafers made of 600-650 µm double side polished silicon are used. The wafers are washed and a wet oxidation is followed.

The first step is the lithography, which includes Hexamethyldisilazane (HMDS) oven, resist coating, exposure, development and descum. The first mask that is used during the exposure is the spiral channel mask. This step follows by hard baking, an oxide etch and later by a resist stripping.

The next step is the lithography of the capillary bore mask. Same step as during the lithography of the fluid channel are carried out.

After the first two lithography steps, the first silicon etching (DRIE) takes place. This result in a etch pattern created by the capillary bore mask. A resist stripping results in that the resist bore mask is removed.

After the removal of the Bore mask, the next silicon etch (DRIE) takes place. This etching results in a etch pattern from the spiral channel mask.

Yet another time, an oxide stripping takes place and in this part of the process, even an oxidation (including standard wash and wet oxidation) is carried out. The final step on this side of the silicon wafer (the back) is a metal deposition, where aluminum is sputtered.

The wafer is then turned around and the rest of the process takes place at the other side (the front).

Lithography is carried out with a five-point star mask for the needles. Also as above, hard baking, an oxide etching and resist stripping are all carried out.

After the lithography of the star mask, a base mask is used for the needles and the same lithography process takes place.

A hard baking and an oxide etch is carried out. This is followed by an isotropic etching, and later by an anisotropic etching to create the pattern of the base mask. After the two etchings, a resist stripping takes place and the resist base mask is removed.

The next step in the process is the oxide etching, followed by the silicon etching (DRIE) that creates the etch pattern of the Star mask.

Thereafter an oxide stripping is performed, followed by an oxidation, an oxide stripping again and a new oxidation. The last step in the process of the silicon wafer is a metal deposition of the back of the wafer. The metal may be e.g. gold.

The silicon wafer is now finished and the Pyrex mask is used to get the transmission line pattern on the Pyrex wafer. Metal deposition on the Pyrex wafer is done by sputtering, and the process ends with the bonding of the Pyrex wafer and the silicon wafer. The bonded wafer stack is thereafter diced into individual sensor components.

The invention claimed is:

1. A microfabricated sensor comprising:
   at least one hollow microneedle for extraction of a sample of bodily fluid, a fluid channel connected to the at least one microneedle for receiving a sample of bodily fluid extracted by the at least one microneedle,
   a microwave transmission line coupled to and extending along at least a portion of the fluid channel so that bodily fluid in the channel forms a dielectric medium in the microwave transmission line, such that the dielectric properties of the fluid in the fluid channel provide an influence on the electrical properties of the transmission line.

2. The sensor according to claim 1 wherein the fluid channel is defined by walls, the microwave transmission line includes a center conductor and a ground plane, the center conductor is located between the walls of the fluid channel, and the walls of the fluid channel are electrically conductive and connected to the ground plane.

3. The sensor according to claim 1 wherein the at least one microneedle includes a capillary bore, and the at least one microneedle is provided with a cap at a distal end for shielding the capillary bore from clogging, whereby at least one opening to the capillary bore is provided in a lateral direction of the microneedle.

4. The sensor according to claim 3 wherein the at least one opening is provided about midways along a longitudinal extension of the microneedle.

5. The sensor according to claim 3 wherein a plurality of openings are provided in a lateral direction, around a circumference of the microneedle.

6. The sensor according to claim 1 wherein the capillary bore of the at least one microneedle and at least part of the fluidic channel is provided with a hydrophilic surface.

7. The sensor according to claim 1 wherein the microneedle comprises a plurality of cutting elements extending along a longitudinal direction of the microneedle.

8. The sensor according to claim 1 wherein the at least one microneedle has a length of 200-1000 µm, and an outer diameter of 50-200 µm.

9. The sensor according to claim 1 wherein the microwave transmission line is at least substantially coextensive with the fluid channel.

10. The sensor according to claim 1 wherein the fluid channel has an extension in a channel plane, the at least one microneedle protrudes in a direction out of the channel plane, and the fluid channel comprises a spiral channel portion.

11. The sensor according to claim 10 wherein the at least one microneedle is arranged at and connected to a central portion of the spiral channel portion.

12. The sensor according to claim 1 comprising a plurality of hollow microneedles.

13. The sensor according to claim 12 wherein the microneedles are distributed along a portion of the fluid channel.

14. The sensor according to claim 1 wherein the microwave transmission line is a coplanar waveguide, a stripline or a microstrip.

15. The sensor according to claim 1 wherein the microwave transmission line comprises a spiral transmission line portion.

16. The sensor according to claim 1 wherein the microwave transmission line is configured for transmission mode measurements.

17. The sensor according to claim 1 wherein the microwave transmission line is configured for transmission mode phase detection.

18. The sensor according to claim 1 wherein the fluid channel has a width and/or height in the range of 10-100 µm.

19. The sensor according to claim 1 wherein the fluid channel has a length in the range of 1-50 mm.

20. The sensor according to claim 1 wherein the fluid channel is microfabricated in a channel plate.

21. The sensor according to claim 20 wherein the at least one microneedle is fabricated in the channel plate.

22. The sensor according to claim 1, wherein the at least one microneedle is at least partly surrounded by a frame structure dimensioned to support the tip of a finger.

23. The sensor according to claim 22 wherein the frame structure dimensioned to support the tip of a finger is a ring shaped structure protruding along the longitudinal direction of the at least one microneedle.

24. The sensor according to claim 1 wherein the microwave transmission line is fabricated in a transmission line substrate plate.

25. The sensor according to claim 1 wherein the microfabricated sensor is a glucose sensor.

26. A method of microfabricating a sensor having at least one hollow microneedle for extraction of a sample of bodily fluid, a fluid channel connected to the at least one microneedle for receiving a sample of bodily fluid extracted by the at least one microneedle, and a microwave transmission line coupled to and extending along at least a portion of the fluid channel so that bodily fluid in the channel forms a dielectric medium in the microwave transmission line, such that the dielectric properties of the fluid in the fluid channel provide an influence on the electrical properties of the transmission line, the method comprising:
  providing a channel wafer, having a first and a second face;
  etching the at least one microneedle on the channel wafer, protruding from the first face of the silicon wafer;
  etching the fluid channel in the second face of the channel wafer;
  providing a transmission line substrate wafer;
  forming the microwave transmission line on the transmission line substrate wafer; and
  assembling the channel wafer and the transmission line substrate wafer such that the microwave transmission line is coupled to and extends along at least the portion of the fluid channel.

27. The method according to claim 26 wherein the channel wafer is a silicon wafer and wherein the transmission line substrate wafer is a glass wafer, assembled by bonding.

28. The method according to claim 26 wherein the at least one microneedle is formed in the channel wafer by deep reactive ion etching.

29. Method of detecting a component in bodily fluid of a patient comprising:
  providing a microfabricated sensor having at least one hollow microneedle for extraction of a sample of bodily fluid, a fluid channel connected to the at least one microneedle for receiving a sample of bodily fluid extracted by the at least one microneedle, and a microwave transmission line coupled to and extending along at least a portion of the fluid channel so that bodily fluid in the channel forms a dielectric medium in the microwave transmission line, such that the dielectric properties of the fluid in the fluid channel provide an influence on the electrical properties of the transmission line;
  extracting the sample of bodily fluid through the at least one microneedle;
  receiving the fluid sample in the fluid channel;
  using the microwave transmission line to perform a swept frequency or pulsed measurement on the fluid sample; and
  detecting the component based on the performed RF measurement.

30. Method according to claim 29 comprising determining the level of the component based on the performed swept frequency or pulsed measurement.

31. Method according to claim 29 wherein the swept frequency or pulsed measurement comprises detecting and/or measuring a phase change.

32. The method according to claim 29 wherein the bodily fluid is blood and/or interstitial fluid.

33. The method according to claim 29 wherein the component is glucose.

34. The method according to claim 29 wherein the swept frequency measurement is performed at a center frequency above 1 GHz.

* * * * *